United States Patent [19]

Perry

[11] Patent Number: 5,108,288

[45] Date of Patent: Apr. 28, 1992

[54] NON-ROTATIONAL PROSTHODONTIC RESTORATION

[76] Inventor: William L. Perry, 1517 Live Oak, Irving, Tex. 75061

[21] Appl. No.: 715,507

[22] Filed: Jun. 14, 1991

[51] Int. Cl.$^5$ .............................................. A61C 8/00
[52] U.S. Cl. .................................... 433/173; 433/174
[58] Field of Search ............... 433/173, 174, 175, 176

[56] References Cited

U.S. PATENT DOCUMENTS

| | | | |
|---|---|---|---|
| 4,854,872 | 8/1989 | Detsch | 433/173 |
| 4,856,994 | 8/1989 | Lazzara et al. | 433/173 |
| 4,955,811 | 9/1990 | Lazzarra et al. | 433/173 |
| 4,976,739 | 12/1990 | Duthie, Jr. | 433/174 |
| 4,988,297 | 1/1991 | Lazzara et al. | 433/173 |
| 4,988,298 | 1/1991 | Lazzara et al. | 433/173 |

Primary Examiner—Cary E. O'Connor
Attorney, Agent, or Firm—David H. Judson

[57] ABSTRACT

A dental prosthodontic restoration includes at least one implant fixture adapted to be implanted in a jawbone of a patient. The implant fixture has a threaded bore axially disposed therethrough and opening centrally through its gingival end. In one embodiment, the restoration includes a standard abutment having an abutment base having a fitting at its inferior end, a socket at its superior end, and a bore axially disposed through the base and opening centrally through the fitting and the socket. The abutment base is supported on the implant fixture, preferably in a non-rotational manner. The restoration further includes an abutment screw having an externally-threaded shaft for mating with the threaded bore of the implant fixture, a male fitting at its superior end having a polygonal cross-section, and a secondary bore opening through the superior end coaxial with and extending toward the shaft. Preferably, a locking sleeve is provided and has an outer periphery formed in a predetermined shape for mating with the superior socket of the abutment base. A bore is axially disposed through the sleeve and has the same polygonal cross-section as the male fitting at the superior end of the abutment screw. When the abutment base, the abutment screw and the locking sleeve are assembled intra-orally in the patient's mouth, the locking sleeve locks the abutment screw to the abutment base to prevent rotation, movement and loosening of the abutment screw. A similar locking mechanism is provided for coping screw.

14 Claims, 2 Drawing Sheets

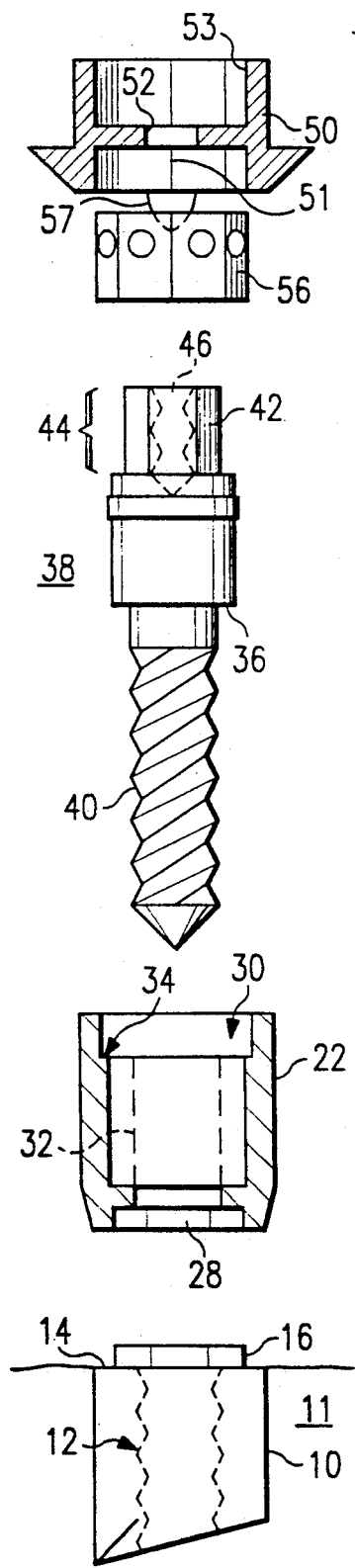
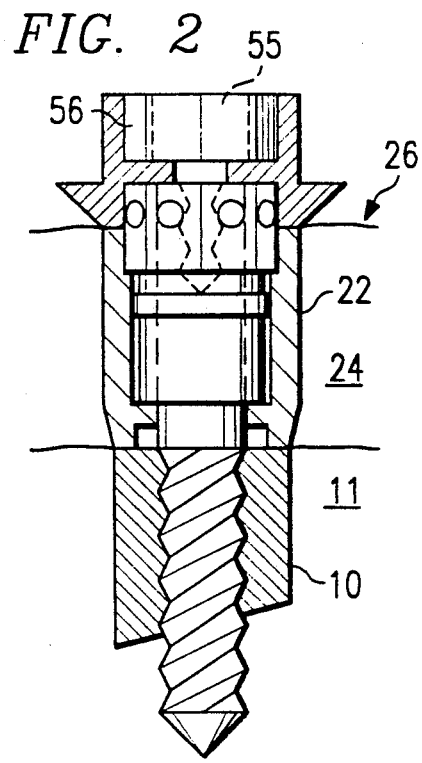
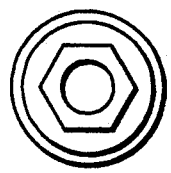
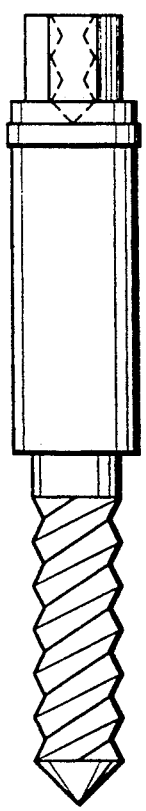
FIG. 1
FIG. 2
FIG. 3A
FIG. 3B

NON-ROTATIONAL PROSTHODONTIC RESTORATION

The present invention relates generally to implant restorative dentistry and more particularly to a prosthodontic restoration system having components that can be optionally assembled in an anti-rotational fashion and in which retention screws used in the system are prevented from loosening or otherwise backing out of their fittings.

BACKGROUND OF THE INVENTION

Prosthodontic restorative systems and techniques are well-known in the prior art. For partially or fully edentulous patients, a dental implant fixture is implanted in a cylindrical bore made in the alveolar ridge crest of a patient's jawbone after the gum tissue has been displaced. The fixture usually includes an internally-threaded cylindrical socket which receives one or more components used for attaching a permanent dental restoration to the fixture. The components typically include an abutment base in the form of a short tubular body having a transverse wall at a first end thereof shaped to mate with the gingival aspect of a transverse surface of the implant fixture. The abutment base has a bore therethrough for receiving an abutment screw used to retain the abutment base to the fixture. A dental restoration, in the form of an anatomical overlay, is adapted to be affixed to the abutment base. One such system is shown in U.S. Pat. No. 4,988,298 to Lazzara et al.

It is also known in the prior art to provide such single-tooth prosthodontic restorations with suitable means for preventing the anatomical overlay from rotating with respect to the remainder of the implant fixture. Such systems are described in U.S. Pat. No. 4,955,811 to Lazzara et al. While the inventions disclosed in the above-identified patents have proven advantageous, such prior art methods and techniques do not address all of the problems associated with permanent dental restoration. One such problem involves the tendency of the various abutment and other retaining and coping screws to reverse or "back-out" of their fittings following installation. Presently, there exists no solution to this problem.

It would therefore be desirable to provide a dental implant restorative system having optional anti-rotational features and wherein retention screws are rigidly secured against rotation to prevent screw reversal during normal use and wear of the system.

BRIEF SUMMARY OF THE INVENTION

It is an object of the present invention to provide an improved non-rotational prosthodontic restoration wherein components can be assembled in an anti-rotational fashion.

It is yet another object of the present invention to provide simple, reliable, cosmetically-attractive and permanent single and multi-tooth restorations which exhibit non-rotational principles.

It is yet a further object of the present invention to provide systems and methods for preventing retention screw reversal in a prosthodontic restoration, such systems and methods being versatile and compatible with various types of implant fixtures and restorative options and procedures.

It is still another object to provide a dental restoration in which all parts are or optionally can be placed in a non-rotational configuration and the screws used in the restoration are prevented from backing out or loosening by a simple geometric screw locking mechanism. Thus, component position cannot be disturbed and cause future inaccuracies.

These and other objects of the invention are provided in a dental prosthodontic restoration comprising at least one implant fixture adapted to be implanted in a jawbone of a patient. The implant fixture typically has a threaded bore axially disposed therethrough and opening centrally through its gingival end. According to the invention, a dental overlay is affixed to the implant fixture generally using either a "standard" abutment (i.e., an abutment having a coping on which the overlay is supported) or a "direct" abutment (i.e., an abutment that supports the overlay itself without any coping). "Standard" and "direct" abutments further come in two (2) basic types: engaging and non-engaging. "Engaging" abutments are actually locked to the implant fixture to prevent relative rotation therebetween; "non-engaging" abutments are not locked to the implant fixture and therefore can rotate with respect thereto.

In one embodiment of the invention, the restoration includes a standard abutment comprising an abutment base having a fitting at its inferior end, a socket at its superior end, and a bore axially disposed through the base and opening centrally through each of the sockets. The abutment base is supported on the implant fixture, preferably in a non-rotational (i.e., engaging) manner. In particular, the superior end of the implant fixture and the inferior end of the abutment base include mated fittings, i.e., a female indentation or a male projection, to enable the abutment base to be attached to the implant fixture. Typically, the superior end of the implant fixture will include a male projection while the inferior end of the abutment base has a female indentation. In this embodiment, the restoration further includes an abutment screw having an externally-threaded shaft for mating with the threaded bore of the implant fixture, a male fitting at its superior end having a polygonal cross-section, and a secondary internally-threaded bore opening through the superior end coaxial with and extending toward the shaft. A locking sleeve is also provided to prevent the abutment screw from loosening or otherwise backing out. The locking screw has an outer periphery formed in a predetermined shape for mating with the superior socket of the abutment base. A bore is axially disposed through the sleeve and advantageously has the same polygonal cross-section as the male fitting at the superior end of the abutment screw. When the abutment base, the abutment screw and the locking sleeve are assembled intra orally in the patient's mouth, the locking sleeve locks the abutment screw to the abutment base to prevent rotation, movement and loosening of the abutment screw and the remainder of the restoration.

In an alternate embodiment of the invention, the restoration includes a direct abutment comprising an abutment base having a fitting at its inferior end, a socket at its superior end, and a bore axially disposed through the base and opening centrally through each of the sockets. No coping is required when a direct abutment is used. As before, the abutment base is supported on the implant fixture, optionally in a non-rotational manner. The restoration also includes an abutment screw having an externally-threaded shaft for mating with the threaded bore of the implant fixture, a male fitting at its superior end having a polygonal cross-section. A locking sleeve is also provided to prevent the abutment screw from loosening or otherwise backing out. When the abutment base, the abutment screw and the locking sleeve are assembled intra-orally in the patient's mouth, the locking sleeve locks the abutment screw to the abutment base to prevent abutment screw rotation. Alternatively, the abutment screw is securely retained relative to the superior socket of the abutment base by filling the space between the socket and the male fitting of the abutment screw with a composite material that hardness upon application.

The use of a locking sleeve that has an outer periphery matched with the superior socket of the abutment base as well as an inner periphery matched to the male fitting of the abutment screw is highly advantageous. A similar locking mechanism is used if desired to lock the coping screw of the restoration to the coping when the standard abutment technique is used.

The foregoing has outlined some of the more pertinent objects of the present invention. These objects should be construed to be merely illustrative of some of the more prominent features and applications of the invention. Many other beneficial results can be attained by applying the disclosed invention in a different manner of modifying the invention as will be described. Accordingly, other objects and a fuller understanding of the invention may be had by referring to the following Detailed Description of the preferred embodiment.

BRIEF DESCRIPTION OF THE DRAWINGS

For a more complete understanding of the present invention and the advantages thereof, reference should be made to the following Detailed Description taken in connection with the accompanying drawings in which:

FIG. 1 is an exploded view showing the various components of a first embodiment of the dental restoration according to the teachings of the present invention, the restoration using a standard abutment;

FIG. 2 is a view of the dental restoration of FIG. 1 shown fully-assembled;

FIGS. 3A-B are plan and elevational views of the preferred structure of the abutment screw used in the dental restoration of FIG. 1;

Similar reference characters refer to similar parts throughout the several views of the drawings.

DETAILED DESCRIPTION

Figure 4A:
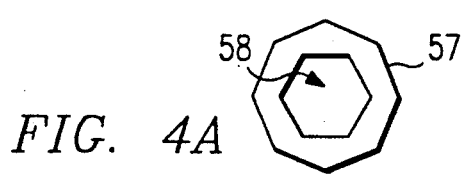
FIGS. 4A-B are plan and elevational views of the preferred structure of the locking sleeve used in the dental restoration of FIG. 1.
Figure 4B:
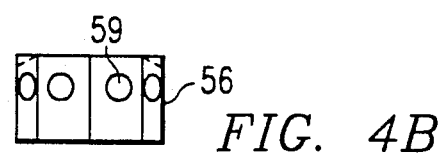

The teachings of the present invention are applicable to single tooth, partially-edentulous, fully-edentulous or fixed-removable restorations. For purposes of simplicity, however, the following description is limited to describing the invention in the context of a single tooth restoration. Referring now simultaneously to FIGS. 1-2, 3A-B and 4A-B, a single tooth standard abutment prosthodontic restoration includes a dental implant fixture 10 which is implanted in a cylindrical bore made in the alveolar ridge crest of a patient s jawbone 11 after the gum tissue has been displaced. A coronal end of the fixture has at its gingival aspect a transverse surface 14 that is substantially flush with the alveolar ridge crest after the fixture is implanted.

The implant fixture 10 has an internally-threaded socket or indentation 12 opening to its gingival surface 14, on which a male annular fitting 16 is fixed. The fitting 16 preferably has a non-circular outer periphery, e.g., hexagonal, surrounding the opening 12. After the implant fixture has osseointegrated with the jawbone of the patient, a standard abutment is attached to the fixture. The abutment comprises an abutment base 22 fitted to the fixture 10 through an opening in the overlying gum tissue 24. The surface of the gum tissue is represented by the numeral 26, and the abutment base 22 has a thickness approximating the thickness of the gum tissue. In the structure shown in FIGS. 1-2, the abutment base 22 has a first female hexagonal socket 28 sized to mate with the male hexagonal fitting 16; alternatively, the abutment base has a male projection and the superior end of the implant fixture has a female indentation. Referring back to the drawings, at its opposite end the abutment base has a second fitting, generally a polygonal (preferably octagonal) socket 30. A bore 32 passes completely through the abutment base 22 between the two female sockets and opens centrally through each of these sockets. The bore has a beveled wall or shoulder 34 for receiving a flange 36 of an abutment screw 38.

The standard abutment screw 38, shown in FIGS. 3A-B, has an externally threaded shaft 40 intended to mate with the internally-threaded socket 12 in the implant fixture 10. When the abutment 22 is fitted to the bone surface 14 with the female indentation 28 embracing the male hexagonal fitting 16, the screw 38 is screwed into the socket 12 until the flange 36 is tight on the shoulder 34. The abutment 22 is then assembled non-rotationally to the implant fixture; however, in certain circumstances it is desirable or at least not problematic to secure the abutment to the fixture in a rotational manner. The standard abutment screw 38 has a preferably male hexagonal fitting 42 at its superior end 44, and a secondary internally-threaded bore 46 opening through the end 44 coaxial with and extending toward the shaft 40. As will be described below, when a "direct" abutment screw is used with a direct abutment no bore 46 is required.

When assembled intra-orally as seen in FIG. 2, the hexagonal fitting 42 of the abutment screw 38 occupies the central volume within the octagonal socket 30, leaving an annular volume that is accessible to other components as will be described. This hexagonal fitting 42 is used to tighten the abutment screw 38 on the implant fixture 10.

The prosthodontic restoration further includes a coping 50 having a bore 52 passing axially therethrough and opening into a preferably polygonal opening 51 at its inferior or lower end. Although not meant to be limiting, preferably the opening has an octagonal shape. According to one important feature of the present invention, the dental prosthodontic restoration includes a locking sleeve 56, best seen in FIGURES 4A-B, for insuring that the abutment screw 38 is nonrotationally secured within the restoration. The sleeve 56 has an outer periphery 57 formed in this example in the same shape (i.e., octagonal) as that of the superior female indentation 30 of the abutment base 22 and the inferior female indentation 51 of the coping. The locking sleeve 56 includes a bore 58 (seen in FIG. 4A) passing axially therethrough and formed in a preferably hexagonal shape. The bore 58 thus precisely fits onto the male hexagonal fitting 42 of the abutment screw 38, while the outer peripheral surface of the sleeve is received securely at one end in the superior female socket 30 (of the abutment base 22) and at the other end in the inferior female socket 51 (of the coping 50). The locking sleeve 56 thus locks the abutment screw to the abutment base, and therefore prevents rotation, movement and loosening of the assembly. This construction significantly reduces errors and Post-seating problems associated with the prior art. The locking sleeve preferably includes one or more transverse holes 59 for facilitating the easy removal of the sleeve. The superior aspect of the sleeve can be inwardly-beveled (as shown in phantom in FIG. 4A) and/or rounded.

Figure 5A:
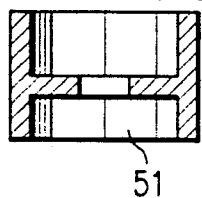
FIGS. 5A-D show various constructions of a coping for use in the standard abutment dental restoration of FIG. 1.
Figure 5B:
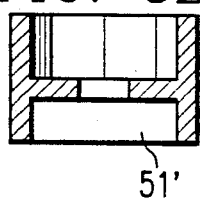
Figure 5C:
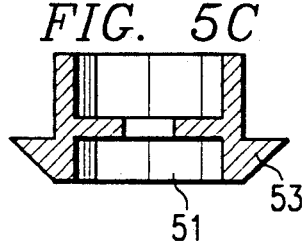
Figure 5D:
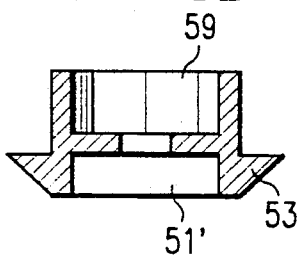

It should be appreciated that the sleeve 56 is designed to lock into the indentation 51 of the coping when the restoration involves a single tooth. However, whenever the restoration is rigidly-splinted to another coping or a natural tooth, it is not required to engage the locking sleeve in the coping. Thus, according to the invention a plurality of different types of copings are provided as best seen in FIGS. 5A-D. For example, the coping used in the standard abutment restoration of FIGS. 1-2 is shown in FIG. 5A and includes the socket 51 for receiving the locking sleeve in an engaging fashion. FIG. 5B shows a non-engaging coping for use when the restoration is rigidly-splined to another coping or a natural tooth. The non-engaging coping of FIG. 5B has an indentation 51' but this indentation does not match the outer peripheral surface of the locking sleeve. FIGS. 5C-D show alternate embodiments of the copings of FIGS. 5A-B, respectively. These alternate coping structures each include a beveled lower edge 53 that facilitates metal finishing and thus prevents damage to coping margins.

Referring now back to the standard abutment restoration shown in FIGS. 1-2, 3A-B and 4A-B, bore 52 of the coping 50 also opens into a female socket 59 at its superior end for receiving a coping screw 55. The coping screw 55 has an externally threaded shaft 57 intended to pass through the bore 52 and to mate with the internally-threaded bore 46 of the standard abutment screw 38. The female socket 59 at the superior end of the coping preferably also receives a locking sleeve 75, similar to the sleeve 56, for locking the coping screw against rotation.

Thus, according to the invention shown in FIGS. 1-2, the abutment base engages into the implant fixture, preventing relative rotation. The abutment screw holds these components together. The superior internal aspect of the abutment base has a polygonal (e.g., octagonal) geometric configuration and the abutment screw has a hexagonal geometric configuration. The locking sleeve is placed between these two components. The abutment base is thus locked to the implant by the inferior configuration and to the abutment screw via the superior internal configuration. Neither the abutment screw nor the abutment base can back-out, loosen, move or rotate.

The standard abutment restoration assembly shown in FIGS. 1-2 is designed for use in all typical restorative situations in which the implant fixture has a geometric anti-rotational configuration at its superior or coronal aspect. In the standard abutment restoration, the dental overlay is formed on the coping which, in turn, is supported by the abutment base.

Figure 6:
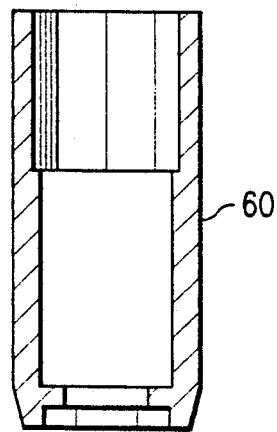
FIG. 6 shows a "direct" abutment for use in an alternate embodiment of the invention.
Figure 7:
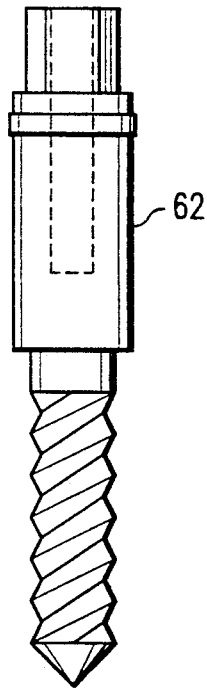
FIG. 7 shows an abutment screw for use with the direct abutment of FIG. 6 in the alternate embodiment of the invention wherein the restoration uses a direct abutment.

The locking sleeve and anti-rotational principles of the invention are likewise suitable when the restoration uses a so-called "direct" abutment, i.e., an abutment that supports the overlay itself without any coping. In such case, a corresponding direct abutment screw is used with the direct abutment and the overlay is fabricated on the direct abutment. FIG. 6 shows a "direct" abutment 60 for use in one such alternate embodiment of the invention, and FIG. 7 shows an abutment screw 62 for use with the direct abutment of FIG. 6. As seen in FIG. 6, the direct abutment 60 has generally the same configuration as the standard abutment of FIG. 1, however, no coping is required. As discussed above, the direct abutment 60 is either engaging or non-engaging with respect to the implant fixture. The direct abutment screw 62 of FIG. 7 is similar in construction to the standard abutment screw except that the bore 46 is not required.

Figure 8:
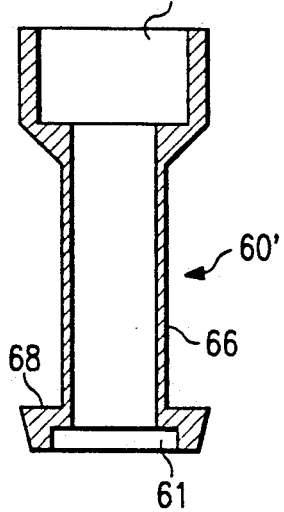
FIG. 8 shows yet another construction of the direct abutment of FIG. 7 having a "shoulder" construction.
Figure 9:
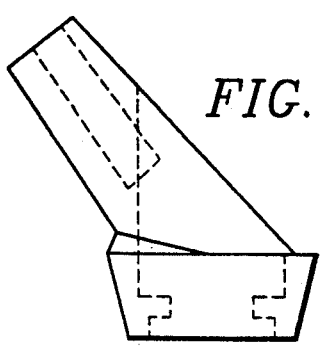
FIG. 9 shows an "angulated" abutment for use in yet another alternate embodiment of the invention.

Referring now to FIG. 8, the direct abutment 60' may alternatively comprise a so-called "shoulder" construction. In particular, direct abutment 60' has a conventional fitting 63 (i.e., either a male projection or a female indentation as shown) for coupling the abutment to the implant fixture either rotationally or anti-rotationally. The abutment 60' also includes the superior socket 64 for receiving the head of the abutment screw and the locking sleeve as previously described. The midsection 66 of the abutment 60' has a relatively thin cross-section relative to the inferior and superior ends. A shoulder 68 is thus formed adjacent the inferior end of the abutment. This construction is advantageous because it provides additional space and volume (surrounding the abutment) for use by the dental professional for optimal placement of restorative material; i.e., porcelain, composite or metal. FIG. 9 shows an "angulated" abutment for use when angled fixture placement is required.

While the locking sleeve assembly is definitely preferred, it is also a feature of the present invention to prevent retention screw reversal by providing a curable composite material for example in the space between the fitting 42 of the abutment screw 38 and the socket 51 of the coping. Such material is generally pliable when applied and thus can be readily manipulated by the dental professional. Upon application, the material hardens and thus prevents rotation of the abutment screw. The composite can also be used to prevent the coping screw from backing out when the standard abutment restoration is used. Preferably, the composite is one similar to a plastic material sold under the name Herculite which is available from the Kerr Company.

Further, as noted above the invention is useful for single unit restoration or fixture restoration bridged to another implant fixture or a natural tooth (with or without a stress breaker in the bridge). Although not shown in detail, it should be appreciated that the abutment base will have a variable height depending on the thickness of the gum tissue. Typically, the abutment base is between 2.0 mm (for aesthetic applications with minimal transmucosal height) to 10.0 mm (for situations with larger transmucosal height). components of the restoration are typically formed of gold, ceramic, titanium or other acceptable material.

Although not described in detail, it should be appreciated that when a standard abutment restoration is used, the system includes other components. For example, in order to create final restoration on the coping 50 (or on a framework formed with a plurality of copings), an impression or so-called transfer coping is first affixed to the abutment screw. Resilient impression material is then applied over the assembly. Once the impression material cures, it is removed. The transfer coping is then removed as well. The system also includes a laboratory analog having a replica of the implant fixture (for a "direct" restoration) or a replica of the abutment base (for a "standard" restoration). The transfer coping is then transferred to the laboratory analog, and the impression is re-fitted to the transfer coping. A core material used to make a rigid model is then fashioned over the impression and formed. The dental overlay is then formed on the rigid model.

It should be appreciated by those skilled in the art that the specific embodiments disclosed above may be readily utilized as a basis for modifying or designing other structures for carrying out the same purposes of the present invention. It should also be realized by those skilled in the art that such equivalent constructions do not depart from the spirit and scope of the invention as set forth in the appended claims.

What is claimed is:

1. A dental prosthodontic restoration, comprising:
   at least one implant fixture adapted to be implanted in a jawbone of a patient, the implant fixture having a threaded bore axially disposed therethrough and opening centrally through its gingival end;
   an abutment having a fitting at its inferior end, a socket at its superior end, and a bore axially disposed therethrough and opening centrally through the fitting and the socket, the abutment being supported on the implant fixture;
   an abutment screw having an externally-threaded shaft for mating with the threaded bore of the implant fixture, a male fitting at its superior end having a polygonal cross-section, and a secondary bore opening through the superior end coaxial with and extending toward the shaft; and
   a locking sleeve having an outer periphery formed in a predetermined shape for mating with the superior socket of the abutment, and a bore axially disposed through the sleeve and having the same polygonal cross-section as the male fitting at the superior end of the abutment screw, wherein when the abutment, the abutment screw and the locking sleeve are assembled intra-orally in the patient's mouth, the locking sleeve locks the abutment screw of the abutment to prevent rotation, movement and loosening of the abutment screw.

2. The dental prosthodontic restoration as described in claim 1 wherein the abutment is a standard abutment for supporting a copying on which a dental overlay is formed.

3. The dental prosthodontic restoration as described in claim 2:
   wherein the coping has a socket at its inferior end, a socket at its superior end, and a bore axially disposed through the coping and opening centrally through each of the sockets of the coping, wherein the inferior end socket of the coping has a predetermined shape for mating with the outer periphery of the locking sleeve and thus preventing rotation of the coping relative to the locking sleeve.

4. The dental prosthodontic restoration as described in claim 2:
   wherein the coping has a socket at its inferior end, a socket at its superior end, and a bore axially disposed through the coping and opening centrally through each of the sockets of the coping, wherein the inferior end socket of the coping has a circular cross-section shape to enable the coping to rotate relative to the locking sleeve.

5. The dental prosthodontic restoration as described in claim 3 or 4 further including:
   a coping screw having a male fitting at its superior end and an externally-threaded shaft for mating with the secondary internally-threaded bore of the abutment screw.

6. The dental prosthodontic restoration as described in claim 5 further including a coping screw locking sleeve for locking the male fitting of the coping screw in the superior end socket of the coping.

7. The dental prosthodontic restoration as described in claim 1 wherein the abutment is a direct abutment for directly supporting a dental overlay.

8. The dental prosthodontic restoration as described in claim 1 wherein the abutment is an angulated abutment.

9. The dental prosthodontic restoration as described in claim 1 wherein the polygonal cross-section of the bore in the locking sleeve is hexagonal.

10. The dental prosthodontic restoration as described in claim 1 wherein the fitting of the abutment is a socket and wherein the implant fixture has a male projection at its superior end for mating therein.

11. The dental prosthodontic restoration as described in claim 10 wherein the male fitting of the implant fixture and the inferior end socket of the abutment each have a polygonal cross-section for preventing rotation of the abutment relative to the implant fixture around a longitudinal axis running successively through the restoration.

12. The dental prosthodontic restoration as described in claim 10 wherein the male fitting of the implant fixture and the inferior end socket of the abutment each have a circular cross-section for allowing rotation of the abutment relative to the implant fixture around a longitudinal axis running successively through the restoration.

13. A dental prosthodontic restoration, comprising:
   at least one implant fixture adapted to be implanted in a jawbone of a patient, the implant fixture having a threaded bore axially disposed therethrough and opening centrally through its gingival end;
   an abutment having a fitting at its inferior end, a socket at its superior end, and a bore axially disposed therethrough and opening centrally through the fitting and the socket, the abutment being supported on the implant fixture;
   an abutment screw having an externally-threaded shaft for mating with the threaded bore of the implant fixture, a male fitting at its superior end having a polygonal cross-section, and a secondary internally-threaded bore opening through the superior end coaxial with and extending toward the shaft; and
   a coping having a socket at its inferior end, a socket at its superior end, and a bore axially disposed through the coping and opening centrally through each of the sockets of the coping, wherein when the coping is placed over the abutment screw a space is formed between the male fitting of the abutment screw and the inferior socket of the coping; and composite material means supported in the space for preventing rotation of the abutment screw.

14. A dental prosthodontic restoration, comprising:

at least one implant fixture adapted to be implanted in a jawbone of a patient, the implant fixture having a threaded bore axially disposed therethrough and opening centrally through its gingival end;

an abutment having a fitting at its inferior end, a socket at its superior end, and a bore axially disposed therethrough and opening centrally through the fitting and the socket, the abutment being supported on the implant fixture;

an abutment screw having an externally-threaded shaft for mating with the threaded bore of the implant fixture, a male pg.31 fitting at its superior end having a polygonal cross-section, and a secondary bore opening through the superior end coaxial with and extending toward the shaft; and means for preventing rotation of the male fitting of the abutment screw relative to the socket at the superior end of the abutment.

* * * * *